United States Patent
Bartl et al.

(10) Patent No.: US 10,393,677 B2
(45) Date of Patent: Aug. 27, 2019

(54) METHOD AND X-RAY APPARATUS FOR GENERATING A PROJECTIVE X-RAY REPRESENTATION OF AN EXAMINATION OBJECT

(71) Applicant: SIEMENS HEALTHCARE GMBH, Erlangen (DE)

(72) Inventors: Peter Bartl, Erlangen (DE); Marcus Radicke, Veitsbronn (DE); Ludwig Ritschl, Erlangen (DE); Sven-Martin Sutter, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 163 days.

(21) Appl. No.: 15/696,840

(22) Filed: Sep. 6, 2017

(65) Prior Publication Data

US 2018/0073995 A1 Mar. 15, 2018

(30) Foreign Application Priority Data

Sep. 14, 2016 (DE) ........................ 10 2016 217 509

(51) Int. Cl.
*G01N 23/04* (2018.01)
*G01N 23/083* (2018.01)
*G01N 23/041* (2018.01)
*G21K 1/06* (2006.01)

(52) U.S. Cl.
CPC ........... *G01N 23/04* (2013.01); *G01N 23/041* (2018.02); *G01N 23/083* (2013.01); *G21K 1/067* (2013.01)

(58) Field of Classification Search
CPC .... G01N 23/04; G01N 23/041; G01N 23/083; G21K 1/067
See application file for complete search history.

(56) References Cited

U.S. PATENT DOCUMENTS

| 2010/0177864 A1 | 7/2010 | Donath et al. |
| 2010/0220834 A1 | 9/2010 | Heismann et al. |
| 2017/0319149 A1* | 11/2017 | Koehler ................ A61B 6/032 |

FOREIGN PATENT DOCUMENTS

EP 1447046 A1 8/2004

OTHER PUBLICATIONS

Ritschl L. et al; "Optimizing Differential Phase Contrast Date for Tomographic Reconstruction";Institut of Medical Physics, University of Erlangen-Nuernberg, Germany; available online https://www.dkfz.de/en/medphysrad/workinggroups/ct/ct_conference_contributions/PhaseContrastCTOptimized Antiderivative _ CTMeeting2012_LudwigRitschl_Poster.pdf; 2012.
Weitkamp T. et al; "X-ray phase imaging with a grating interferometer"; Optics Express; vol. 13; No. 16; pp. 6296-6304; Aug. 8, 2005.

(Continued)

*Primary Examiner* — Mark R Gaworecki
(74) *Attorney, Agent, or Firm* — Laurence Greenberg; Werner Stemer; Ralph Locher

(57) ABSTRACT

A method and an X-ray apparatus generate a projective X-ray representation of an examination object. Two projective images obtained from a phase contrast measurement are adapted to each other in respect of their representation format and a result image is generated by combining the adapted images. The result image allows extensive separation of different structures in the examination object that is used.

18 Claims, 4 Drawing Sheets

(56) References Cited

OTHER PUBLICATIONS

Kottler C. et al.; "A two-directional approach for grating based differential phase contrast imaging using hard x-rays", Optics Express vol. 15, No. 3, . Feb. 5, 2007, pp. 1175-1181.
Pfeiffer F. et al., "Hard X-ray dark-field imaging using a grating interferometer", Nature Materials, vol. 7, No. 2; Feb. 2008, pp. 134-137; ISSN:1476-1122; DOI: 10.1038/nmat2096; XP55003146; 2008.

* cited by examiner

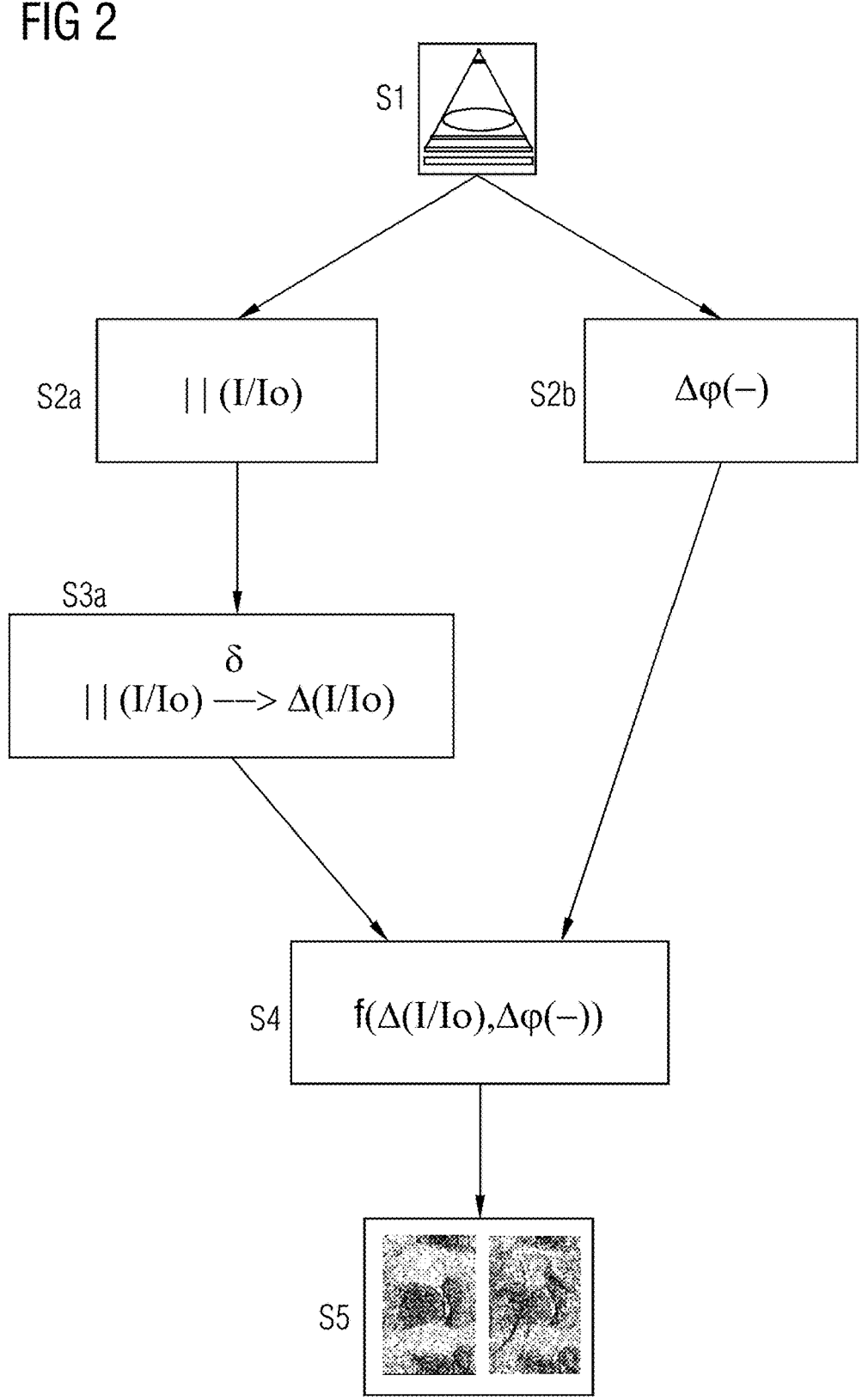

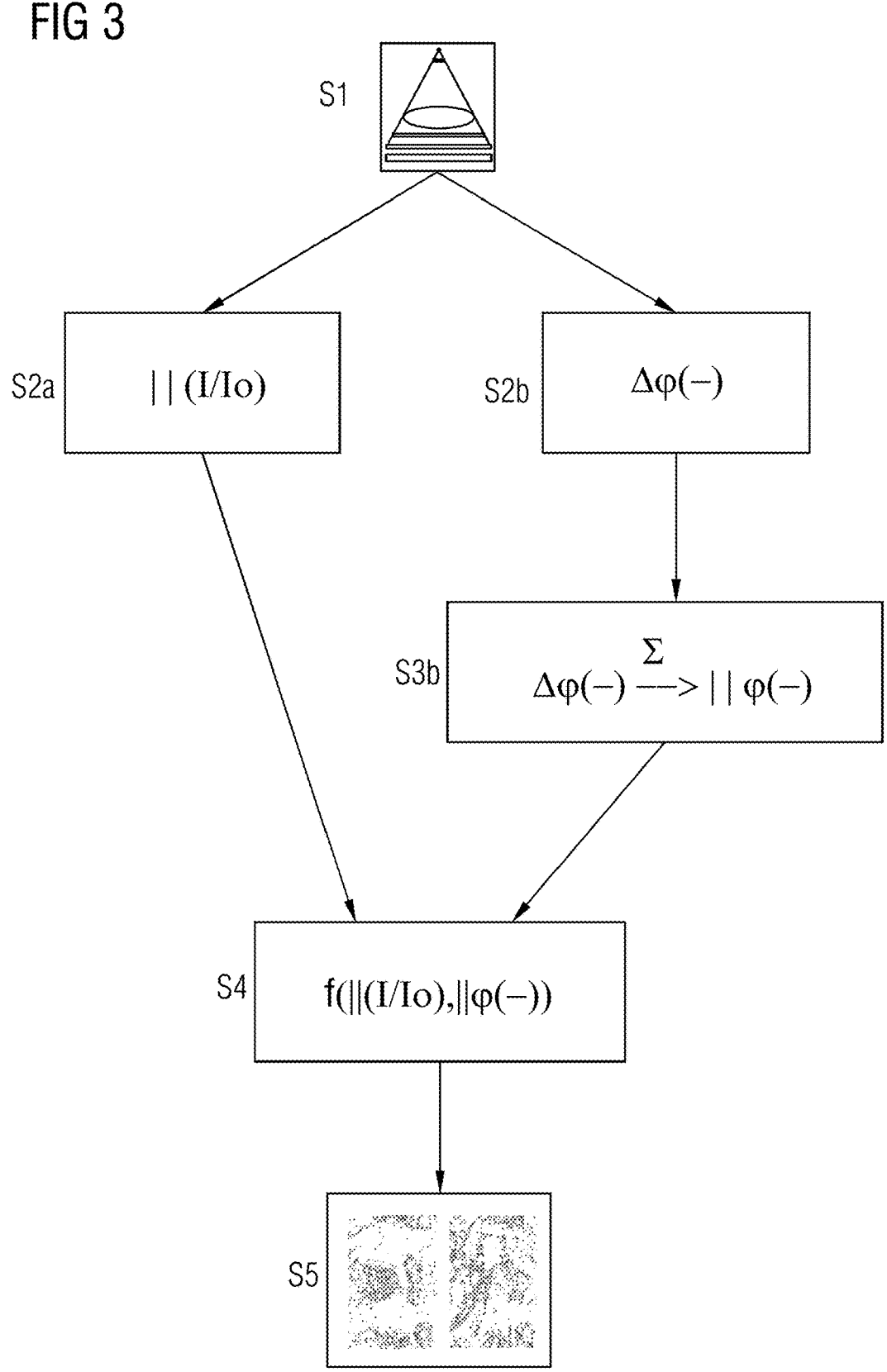

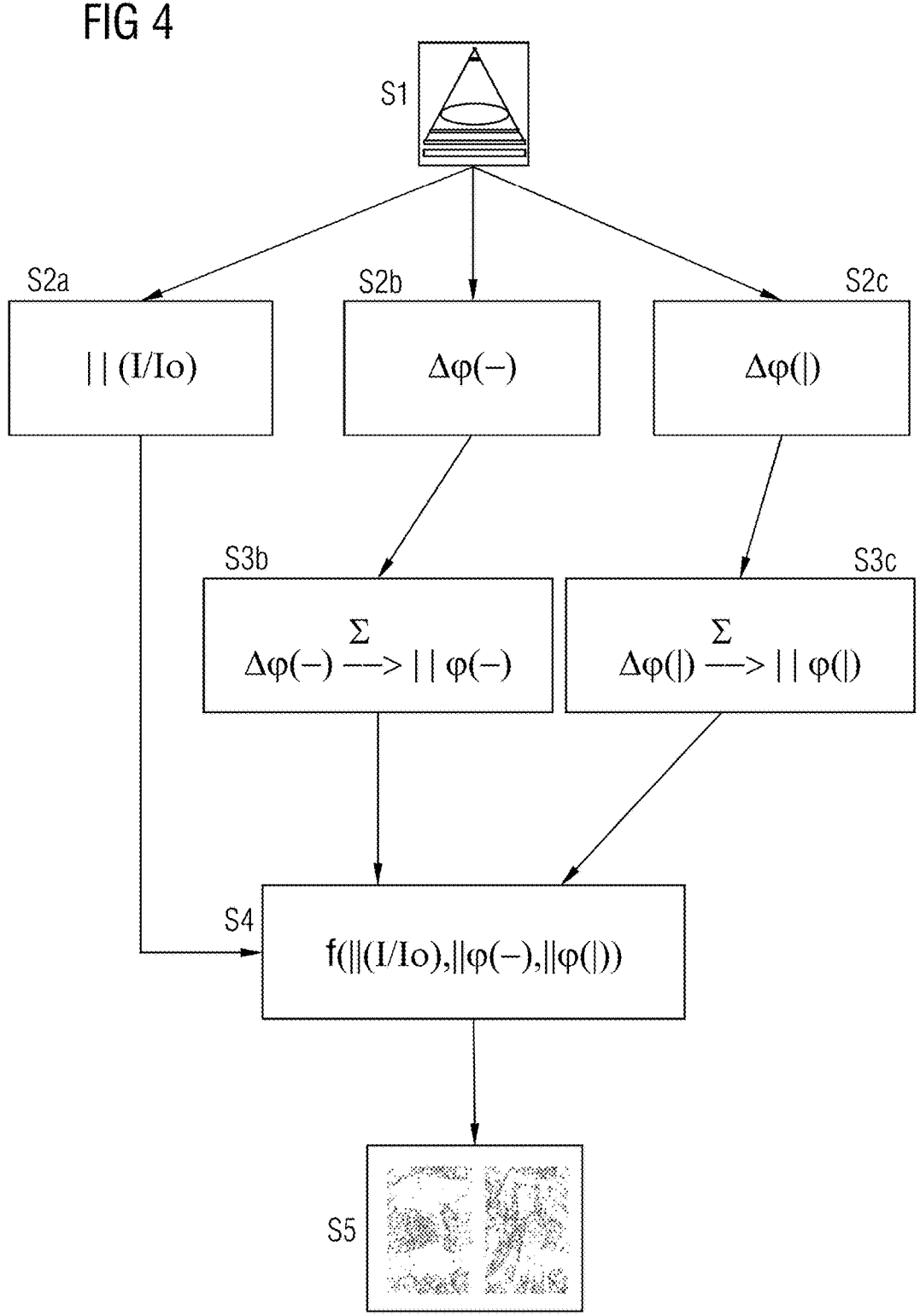

METHOD AND X-RAY APPARATUS FOR GENERATING A PROJECTIVE X-RAY REPRESENTATION OF AN EXAMINATION OBJECT

CROSS-REFERENCE TO RELATED APPLICATION

This application claims the benefit, under 35 U.S.C. § 119, of German patent application DE 10 2016 217 509.2, filed Sep. 14, 2016; the prior application is herewith incorporated by reference in its entirety.

BACKGROUND OF THE INVENTION

Field of the Invention

The invention relates to a method and an X-ray apparatus for generating a projective X-ray representation of an examination object using a radiator-detector system with a Talbot-Lau grating arrangement and a linear phase grating, an absorption image and a differential phase contrast image being ascertained.

Such methods and projective X-ray apparatuses are generally known. Interferometric X-ray imaging (IR) is a variant of phase contrast imaging and is based on the inclusion of at least one phase grating (G1) in an X-ray imaging system. Preferably also included in the ray path of the X-ray imaging system is a source grating (G0) for generating sufficient dose rate and quasi-coherent radiation, and if applicable an analysis grating (G2) for measuring the interference pattern generated by the phase grating with a relatively coarsely segmented detector after the phase grating. By measuring the interference pattern behind the phase grating, it is possible to ascertain three image signals, namely a conventional absorption image, a dark-field image, and a differential phase contrast image. Concerning this, reference is made e.g. to the publication "Hard X-ray Dark-Field Imaging Using a Grating Interferometer", F. Pfeiffer et al., Nature Materials 7 (2008).

One problem associated with this projection-based X-ray imaging is that structures such as e.g. bones, blood vessels and organs in the radiographed examination object are often difficult to differentiate due to mutual superimposition.

Tomographic methods providing sectional images that are as far as possible superimposition-free, e.g. computer tomography or tomosynthesis, represent one possible solution for reducing these structural superimpositions. However, the advantages of purely projective imaging are lost in this case, since the tomographic methods are relatively resource-intensive and also generate higher radiation exposure from one or a small number of spatial angles than a purely projective scan.

SUMMARY OF THE INVENTION

The object of the invention is to find means by which it is possible to separate the information content of purely projective imaging information which was recorded using the method described in the introduction, and to create a result image of a structure of an examination object which is largely free of other structures. For example, to generate a representation of soft parts without bone superimposition and vice versa from an interferometric measurement.

This object is achieved by the features in the independent claims. Advantageous developments of the invention are the subject matter of sub claims.

The inventors discovered that in the lower range of diagnostically relevant energy for X-ray imaging, i.e. using X-ray spectra up to approximately 70 keV acceleration voltage, the phase signal and the absorption signal contain complementary information, since primarily photoelectric effect and Compton effect contribute to the generation of the image signal in this case. It is therefore possible by means of a weighted linear combination of both images to represent individual materials such as bones and soft parts separately without any need for exposure to different energy spectra as is required in the case of "dual-energy" imaging.

Since the phase information that has been ascertained is available in differential format whereas the absorption information exists in absolute values, the phase image and the absorption image must be converted into the same representation format before any combination. This can be achieved by derivation of the absorption image, preferably perpendicular to the alignment of the grating lines of the phase grating for the phase imaging. Alternatively, an integration of at least one phase image is performed. It is also preferably possible for two phase images to be recorded with reciprocally rotated phase gratings, and both integrated perpendicular to the grating lines and amalgamated using a two-dimensional integration. This image with absolute image information can then be processed or linearly combined with the full absorption image to provide a result image.

A particular advantage of the method described here is that further information can be generated from the data which is produced by a typical interferometric measurement using a single X-ray spectrum, without requiring additional measurements. Therefore the information for an absorption image and at least one phase image is obtained from one interferometric measurement using one energy range, and a result image which allows different materials to be separated is generated from these two information elements. In order to allow reciprocal processing of the image data, it is however necessary to adapt one of the images in respect of its representation format, i.e. absolute or differential, to the other by means of integration or differentiation.

In accordance with this inventive idea, in a general basic variant, the inventors propose a method containing the following method steps for generating a projective X-ray representation of an examination object:

a) performing an interferometric projective imaging using a radiator-detector system with a Talbot-Lau grating arrangement with a first linear phase grating with a first alignment, b) ascertaining a projective absorption image with absolute absorption values in absolute representation format, c) ascertaining a first projective differential phase contrast image with differential phase contrast values in differential representation format, d) adapting the representation format of one of the ascertained images to the other image respectively, e) generating at least one new result image by combining an unmodified image with an image which has been adapted in respect of its representation format, and f) storing and/or outputting at least one result image.

It should be noted that the term combination implies a mathematical computation of image pixels of the unmodified image and of the image that has been adapted in respect of its representation format in the sense of a computing combination, at least one newly computed result image being produced. The simple adjacently disposed representation of different images in the same representation format is not considered a combination within the meaning of the invention.

In a first variant, the absorption image is adapted to the phase image, wherein for the purpose of adapting the representation format of the absorption image, spatial derivatives are formed on a pixel-by-pixel basis perpendicular to the first alignment of the grating lines of the at least one phase grating, and the differential absorption image produced thereby is combined with the differential phase contrast image.

In a second variant, the ascertained phase image can be adapted to the absorption image using unidimensional integration, wherein for the purpose of adapting the representation format of the differential phase contrast image, absolute values are formed by integration on a pixel-by-pixel basis perpendicular to the first alignment of the grating lines, and the absolute phase contrast image produced thereby is combined with the absolute absorption image.

One problem associated with such unidimensional integrations of phase images is that linear artifacts are often produced. In order to prevent this, a second phase image is ascertained using a phase grating which is aligned in a second direction, preferably perpendicular to the alignment of the first phase grating.

Accordingly, a third variant of the method proposes that provision is additionally made for ascertaining a second projective differential phase contrast image with differential phase contrast values in differential representation format using a phase grating which is aligned in a second direction.

For the purpose of ascertaining the two phase images using differently oriented phase gratings, the first phase grating can normally be rotated for the second measurement, or a second phase grating having a different alignment can be used instead of the first phase grating for the purpose of ascertaining the second phase contrast image.

The orientation of two phase gratings in respect of their grating lines is preferably aligned such that they run perpendicular to each other.

If an absorption image with absolute image values is ascertained and two phase contrast images with differential image values are ascertained using respectively different alignments of the generating phase gratings, then:
  a) the two differential phase contrast images can each be converted into absolute phase contrast images by means of unidimensional integration perpendicular to the alignment of the generating phase gratings, and
  b) the result image can be computed from the absorption image and the absolute phase contrast images by means of pixel-by-pixel weighted combination.

As an alternative to the aforementioned variant in which unidimensional integration is performed twice, it is also possible to proceed as follows:
  a) the differential phase contrast images can be converted into an absolute phase contrast image by means of two-dimensional integration perpendicular to the alignments of the generating phase gratings, and
  b) the result image can be computed from the absolute absorption image and the absolute phase contrast image by means of pixel-by-pixel combination.

The invention also proposes use of a polynomial, preferably of the degree 1 to 3, for the purpose of combining the images. In this context, polynomial factors previously ascertained in the context of calibration can be used in the chosen polynomial.

If the interference pattern generated by the phase grating is read out by an analysis grating with subsequent detector, this can be performed by so-called phase stepping, in which one of the gratings (preferably the analysis grating) is displaced in a step-by-step manner and a measurement is taken after each step. In total, at least three measurements per pixel must be performed in order to detect the phase shift that is present at the pixel concerned. Accordingly, it is proposed that the phase contrast measurement is performed by phase stepping one of the gratings used.

As an alternative to phase stepping, it is also possible to use a high-resolution detector which is able by virtue of its high resolution directly to analyze the intensity modulation of the interference pattern generated by the phase grating. It is possible to dispense with an analysis grating in this case. Accordingly, it is proposed that the phase contrast measurement is performed by using a detector whose resolution lies in the range of grating spacings of an analysis grating.

It is moreover possible to ascertain the absorption image directly by a measurement in the absence of the source grating and/or the phase grating and/or the analysis grating. However, it is preferably possible to use the measurements already available from ascertaining the phase shift, and to ascertain the absorption image from the sum of the intensity measurements of the phase contrast measurement.

Furthermore, with regard to an optimized arrangement of the gratings in relation to the examination object, it is proposed to position the phase grating between the radiator and the examination object.

In addition to the inventive method, the inventors also propose an X-ray apparatus for generating a projective X-ray representation of an examination object, the apparatus having at least the following features:
  a) a radiator-detector system for X-ray examination of the examination object arranged in a ray path,
  b) a Talbot-Lau grating arrangement in the ray path, with a first linear phase grating with a first alignment,
  c) a control and computing unit with a memory containing program code which during operation is used for the purpose of controlling the X-ray apparatus and for data processing of the signals received from the detector, wherein X-ray representations of the examination object are also generated.

According to the invention, the memory of the control and computing unit also stores program code which during operation performs the method steps of one of the preceding method claims.

The invention is described in greater detail below with reference to preferred exemplary embodiments and the figures, in which only those features required for an understanding of the invention are illustrated. The following reference signs and abbreviations are used here: D: detector; dx: step size in the context of "phase stepping"; F: focus; f( ) combination function; G1: phase grating; G2: system grating; G0: source grating; E1, E2: result images; E: integration; O: examination object; P: program code; R: control and computing unit; S: ray path; S1-S5: steps of the inventive method; δ: differentiation; Δφ(|): differential phase contrast image with vertical grating orientation; Δφ(–): differential phase contrast image with horizontal grating orientation; Δ(I/Io): differential absorption image; ‖φ(|): phase contrast image with absolute values with vertical grating orientation; ‖φ(–): phase contrast image with absolute values with horizontal grating orientation; ‖(I/Io): absorption image in absolute values.

Other features which are considered as characteristic for the invention are set forth in the appended claims.

Although the invention is illustrated and described herein as embodied in a method and X-ray apparatus for generating a projective X-ray representation of an examination object, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a method flow chart of the method according to the invention, with standardization of the representation format by differentiation of the absorption image;

FIG. 3 is a method flow chart of the method according to the invention, with standardization of the representation format by means of linear unidimensional integration of the phase contrast image; and FIG. 4 is a method flow chart of the method according to the invention, with standardization of the representation format by means of linear unidimensional integration of two phase contrast images with different grating orientations, these specifically being arranged perpendicular to each other.

DETAILED DESCRIPTION OF THE INVENTION

Figure 1:
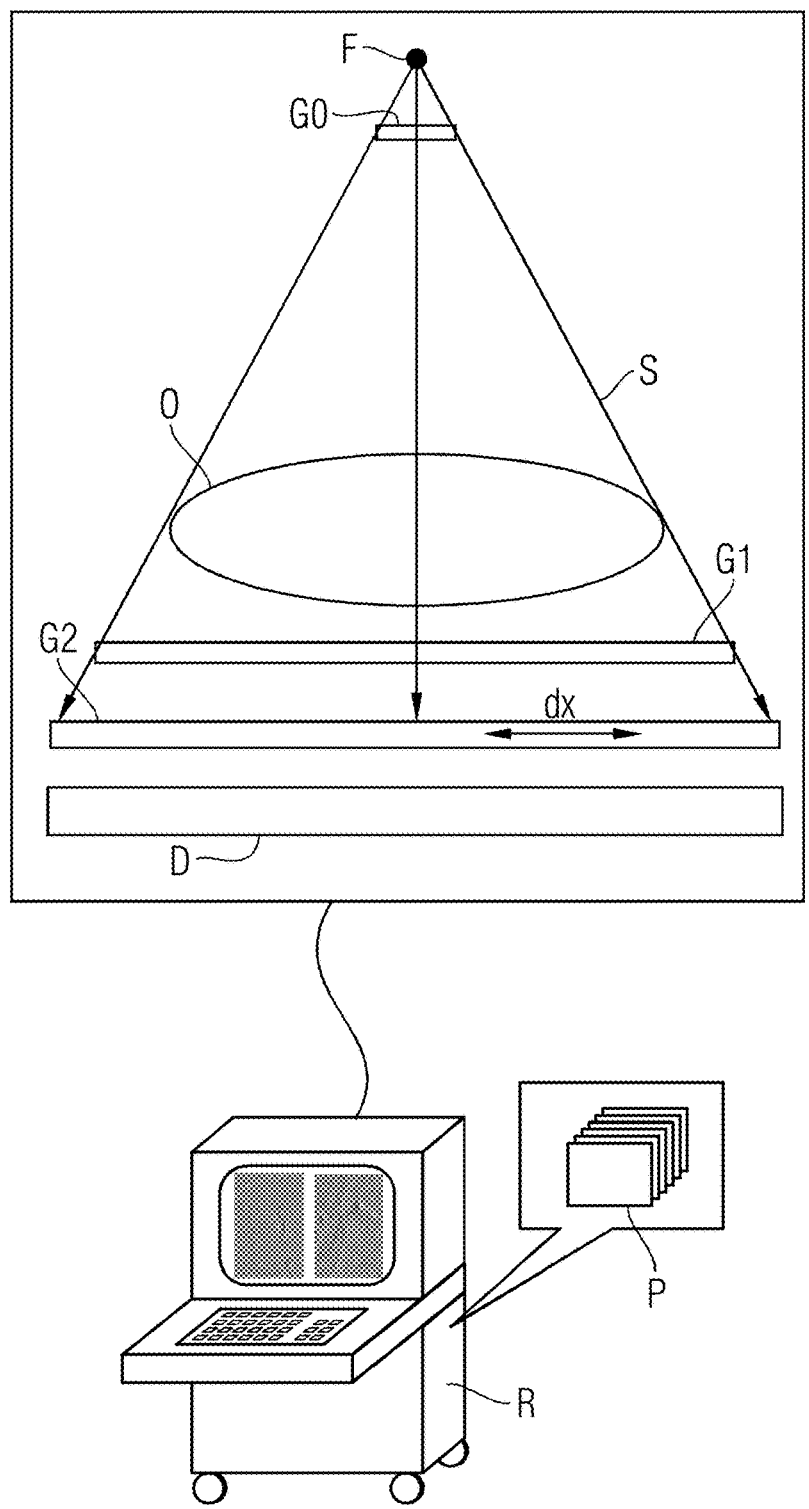
FIG. 1 is an illustration showing a schematic representation of an X-ray apparatus according to the invention.

Referring now to the figures of the drawings in detail and first, particularly to FIG. 1 thereof, there is shown a schematic representation of an exemplary X-ray apparatus according to the invention, having a radiator-detector system which consists of a focus F of an X-ray tube (not shown in further detail) and a detector D for detecting the X-radiation emitted in the ray path S. The ray path S is schematically illustrated by the central ray and the two circumferential rays. In addition, three X-ray gratings corresponding to a Talbot-Lau grating arrangement are placed in the ray path S, a source grating G0 being situated directly at the focus F and generating a quasi-coherent ray bundle. This quasi-coherent ray bundle strikes the subsequent examination object O according to the formation of the ray path S, the examination object O interacting with the X-radiation. The phase grating G1 follows thereupon, and forms an interference pattern which is measured on a pixel-by-pixel basis by step-by-step displacement (phase stepping) of the analysis grating G2 and use of the subsequent detector D.

Control of the radiator-detector system using the X-ray gratings in order to perform the "phase stepping", and evaluation of the measurement results are effected by means of a control and computing unit R, which has a memory containing program code P that performs the customary projective phase contrast measurement and absorption measurement, including the imaging, during operation.

In addition to this, program code P which performs the steps of the inventive method described above is also held in the X-ray apparatus. In particular, program code can also be stored and the X-ray apparatus so configured as to perform a method for projective imaging as described below with reference to FIGS. 2 to 4.

If an absorption image and a phase contrast image are generated using a projective X-ray apparatus with a Talbot-Lau grating arrangement, it is inventively possible to combine, preferably linearly, the absorption image with the phase contrast image. However, since the representation format of the absorption image consists of absolute values while the representation format of the phase contrast image consists of differential values, it is necessary to adapt these representation formats to each other before combination, i.e. either to identify the derivative of the absolute values of the absorption image or to integrate the differential values of the phase contrast image.

FIG. 2 shows a method flow chart, in which the standardization of the representation format is effected by linear unidimensional differentiation of the absorption image in accordance with the invention. Accordingly, in a first step S1, a scan of the examination object takes place using a single X-ray spectrum, the phase grating being adjusted to a single X-ray energy. Therefore the absolute values of an absorption image $\|(I/Io)$ are ascertained in the step S2a and the differential values of a phase contrast image $\Delta\varphi(-)$ are ascertained in the step S2b.

In order to adapt the representation format, in the step S3a, differential values of the absorption are formed from the absolute values of the absorption image by means of differentiation $\delta$ (forming a derivative $d(I/Io)/dx$) perpendicular to the alignment of the grating lines of the phase grating used for the phase contrast image) and the differential absorption image $\Delta(I/Io)$ is generated. In the step S4, provision is made for combining, preferably in a linear manner, the two differential images $f(\Delta(I/Io), \Delta\varphi(-))$ to form at least one result image, which is then stored for further processing and/or displayed in the step S5.

For the purpose of this and the other inventive methods described here, provision can additionally be made for the X-ray apparatus, supported by corresponding program code, to vary the weighting parameters of the combination function $f(\ )$ or the polynomial factors of an alternatively used polynomial function for the output of different result images.

In a further variant of the method according to the invention, the standardization of the representation format can also be effected by a linear unidimensional integration of the phase contrast image. An exemplary method flow chart for this is illustrated in FIG. 3. In this case, in the step S1, a scan of the examination object is again performed using a single X-ray spectrum, the phase grating that is used being adjusted to a single X-ray energy. The absolute values of an absorption image $\|(I/Io)$ are identified in the step S2a and the differential values of a phase contrast image $\Delta\varphi(-)$ are ascertained in the step S2b.

In order to adapt the representation format, in the step S3b, integrals—represented by the symbol $\Sigma$—are formed perpendicular to the alignment of the grating lines of the phase grating that is used, and the absolute values of the phase contrast image $\|\varphi(-)$ are computed thus from the differential image values of the originally ascertained phase contrast image $\Delta\varphi(-)$. Therefore both representations are available in absolute values and can be combined with each other, this occurring in the step S4. In the step S5, the at least one result image thereby produced can then be stored for further processing and/or output.

The method outlined in FIG. 3 is nonetheless associated with the problem that line artifacts often occur as a result of the purely unidimensional integration. Prevention of such line artifacts can be achieved by a two-dimensional integration. According to the invention, a special variant also provides for a phase contrast image to be measured twice, wherein the alignments of the phase grating used here are preferably independent of each other, i.e. perpendicular to each other. For example, the phase grating can be rotated by 90° between the phase contrast measurements.

A corresponding method flow chart for this purpose is illustrated in FIG. 4. In contrast with the method according to FIGS. 2 and 3, provision is additionally made in the step S1 for generating a further phase contrast image using a phase grating which is rotated by 90° relative to the first phase contrast image. The alignment of the source grating and the analysis grating—where present—must obviously also be rotated, such that all X-ray gratings are identically aligned. It is also possible in principle to rotate the entire radiator-detector system including the Talbot-Lau grating arrangement.

Therefore an absorption image $\|(I/Io)$ is generated with absolute image values in the step S2a, a differential phase contrast image $\Delta\varphi(-)$ is generated with e.g. horizontal grating orientation in the step S2b, and a further differential phase contrast image $\Delta\varphi(|)$ is generated with e.g. vertical grating orientation in the step S2c. In the steps S3b and S3c, the differential images are integrated in a direction perpendicular to the alignment of the phase grating used in each case, and the phase contrast images $\|\varphi(-)$ and $\|\varphi(|)$ now consisting of absolute image values are obtained. Since the three available images have now been standardized in respect of their representation format to absolute values, at least one combination $f(\|(I/Io), \|\varphi(-), \|\varphi(|))$ can be computed as a result image in the step S4. The result image is then stored and/or output in the step S5.

In summary, the invention proposes a method and an X-ray apparatus for generating a projective X-ray representation of an examination object, wherein two projective images obtained from a phase contrast measurement are adapted to each other in respect of their representation format and a result image is generated by combining the adapted images, the result image allowing extensive separation of different structures in the examination object that is used.

Although the invention is illustrated and described in detail with reference to the preferred exemplary embodiment, the invention is not restricted by the examples disclosed herein, and other variations may be derived therefrom by a person skilled in the art without thereby departing from the scope of the invention. In particular, the invention is not restricted to the combinations of features specified below, but other combinations and partial combinations which are obvious to a person skilled in the art can also be formed from the features disclosed.

The invention claimed is:

1. A method for generating a projective X-ray representation of an examination object, which comprises the following method steps of:
    performing an interferometric projective imaging using a radiator-detector system with a Talbot-Lau grating configuration having a first linear phase grating with a first alignment;
    ascertaining a projective absorption image with absolute absorption values in absolute representation format;
    ascertaining a first projective differential phase contrast image with differential phase contrast values in differential representation format;
    adapting the representation format of one of the ascertained images to the other image respectively;
    generating at least one new result image by combining an unmodified image with an image which has been adapted in respect of its representation format; and
    storing and/or outputting the at least one result image.

2. The method according to claim 1, wherein for adapting the absolute representation format of the projective absorption image, forming spatial derivatives on a pixel-by-pixel basis perpendicular to the first alignment of grating lines of the first linear phase grating, and a differential absorption image produced thereby is combined with the first projective differential phase contrast image.

3. The method according to claim 1, wherein for adapting the differential representation format of the first projective differential phase contrast image, forming absolute values by integration on a pixel-by-pixel basis perpendicular to the first alignment of grating lines, and an absolute phase contrast image, produced thereby is combined with the projective absorption image.

4. The method according to claim 1, which further comprises ascertaining a second projective differential phase contrast image with differential phase contrast values in the differential representation format using the first linear phase grating which is aligned in a second direction.

5. The method according to claim 4, wherein for ascertaining the second projective differential phase contrast image, rotating the first linear phase grating.

6. The method according to claim 4, wherein for ascertaining the second projective differential phase contrast image, using a second phase grating with a different alignment instead of the first linear phase grating.

7. The method according to claim 4, wherein a second alignment of the first linear phase grating runs perpendicular to the first alignment of the first linear phase grating.

8. The method according to claim 4, which further comprises:
    ascertaining the projective absorption image with absolute image values and the first and second projective differential phase contrast images, $\Delta\varphi(|))$ with differential image values using respectively different alignments of generating phase gratings;
    converting the first and second projective differential phase contrast images, $\Delta\varphi(|))$ into absolute phase contrast images, $\|\varphi(-))$ by means of unidimensional integration perpendicular to an alignment of the generating phase gratings; and
    computing the at least one result image from the projective absorption image and the absolute phase contrast images, $\|\varphi(-))$ by means of pixel-by-pixel weighted combination.

9. The method according to claim 4, which further comprises:
    ascertaining the projective absorption image with absolute image values and the first and second projective differential phase contrast images with differential image values using respectively different alignments of generating phase gratings;
    converting the first and second projective differential phase contrast images into an absolute phase contrast image by means of two-dimensional integration perpendicular to alignments of the generating phase gratings; and
    computing the at least one result image from the absolute absorption image and the absolute phase contrast image by means of pixel-by-pixel combination.

10. The method according to claim 1, which further comprises using a polynomial for combining) images.

11. The method according to claim 10, which further comprises using polynomial factors previously ascertained in a context of calibration in a chosen polynomial.

12. The method according to claim 1, which further comprises performing a phase contrast measurement by means of "phase stepping" one of gratings that is used.

13. The method according to claim 12, which further comprises performing the phase contrast measurement by using a detector whose resolution lies in a range of grating spacing's of an analysis grating.

14. The method according to claim 12, which further comprises ascertaining the absorption image from a sum of intensity measurements of the phase contrast measurement.

15. The method according to claim 1, which further comprises recording the projective absorption image in an absence of the first linear phase grating in a ray path.

16. The method according to claim 1, which further comprises positioning the first linear phase grating between a radiator and the examination object.

17. The method according to claim 1, which further comprises using a polynomial, being a degree 1 to 3, for combining the images.

18. An X-ray apparatus for generating a projective X-ray representation of an examination object, the X-ray apparatus comprising:
- a radiator-detector system for X-ray examination of the examination object disposed in a ray path and having a detector;
- a Talbot-Lau grating configuration disposed in the ray path and having a first linear phase grating with a first alignment; and
- a control and computing unit with a memory containing program code which is used during operation for controlling the X-ray apparatus and for data processing of signals received from said detector, wherein X-ray representations of the examination object are generated, said memory of said control and computing unit storing the program code which during operation further performs method steps according to claim 1.

* * * * *